United States Patent

Wyatt et al.

Patent Number: 6,078,549
Date of Patent: Jun. 20, 2000

[54] REST PATTERN TIMING SYSTEM

[75] Inventors: Patrick Wyatt, Monterey, Calif.; F. Murray Jarman, Boynton Beach, Fla.; S. Regan O'Reilly, Vero Beach, Fla.; Monique F. Jarman, Boynton Beach, Fla.

[73] Assignee: RMP, Inc., Boynton Beach, Fla.

[21] Appl. No.: 09/020,154

[22] Filed: Feb. 7, 1998

Related U.S. Application Data

[63] Continuation-in-part of application No. 08/444,242, May 18, 1995.

[51] Int. Cl.[7] .......................... G04B 47/00; G04C 17/00; G04F 8/00; G08B 23/00
[52] U.S. Cl. .............................. 368/10; 368/69; 368/110; 200/DIG. 2; 340/575
[58] Field of Search ............................ 368/69, 107–113, 368/276, 10, 11; 200/DIG. 2, 61.58 R; 307/116; 340/573, 575

[56] References Cited

U.S. PATENT DOCUMENTS

| | | |
|---|---|---|
| 2,486,591 | 11/1949 | Ferrante . |
| 3,209,529 | 10/1965 | Hetzel . |
| 3,226,501 | 12/1965 | Seserman . |
| 3,548,812 | 12/1970 | Paine . |
| 3,700,835 | 10/1972 | Rackson . |
| 3,944,843 | 3/1976 | Vaz Martins . |
| 4,059,830 | 11/1977 | Threadgill . |
| 4,063,111 | 12/1977 | Dobler et al. . |
| 4,069,659 | 1/1978 | Harris et al. . |
| 4,361,834 | 11/1982 | King .................................... 340/575 |
| 4,493,043 | 1/1985 | Ferrath .................................. 364/565 |
| 4,526,479 | 7/1985 | Harris ................................... 368/284 |
| 4,652,141 | 3/1987 | Arai ...................................... 368/287 |
| 4,681,462 | 7/1987 | Lloyd ...................................... 368/69 |
| 4,999,772 | 3/1991 | Bowman et al. . |
| 5,088,072 | 2/1992 | Fitzmorris ............................. 368/69 |
| 5,124,960 | 6/1992 | Miller et al. . |
| 5,377,170 | 12/1994 | Blaylock et al. . |
| 5,479,939 | 1/1996 | Ogino . |
| 5,481,506 | 1/1996 | Kita . |
| 5,493,276 | 2/1996 | Alvira .................................... 340/576 |
| 5,520,176 | 5/1996 | Cohen . |
| 5,871,406 | 2/1999 | Worrell .................................. 473/221 |

*Primary Examiner*—Vit Miska
*Attorney, Agent, or Firm*—Quarles & Brady LLP

[57] ABSTRACT

A sleep pattern timing apparatus for a user to record time before onset of sleep and to separately record sleep time to assist in the diagnosis and treatment of sleeping disorders can include a timer for recording awake time and sleep time of the user and preferably a plurality of switches such as a galvanic skin response switch and a tactile plunger-type switch electrically connected to the timer so that the timer records sleep time when at least one switch is released. Using an awake timer subsystem, the apparatus can also begin recording awake time when all switches are concurrently actuated and discontinues recording of awake time when at least one switch is released. A plurality of switches can reduce the opportunity for false actuation. The apparatus can be housed in a hand held housing to fall away when released to further reduce false actuation. The apparatus may be attached to the user with a wrist band for easy retrieval during sleep interruptions.

20 Claims, 3 Drawing Sheets

REST PATTERN TIMING SYSTEM

CROSS-REFERENCE TO RELATED APPLICATION

This application is a continuation-in-part of U.S. patent application Ser. No. 08/444,242, filed May 18, 1995.

FIELD OF THE INVENTION

This invention relates to a method and apparatus for measuring human resting and sleep characteristics and parameters. More particularly, this invention relates to systems for generally measuring sleep and awake times during resting periods.

BACKGROUND OF THE INVENTION

Statistics indicate that sleeping disorders such as insomnia plague a significant percentage of the world's population—70 million in the United States alone. Chronic insomnia is believed to be a problem for 15 to 30 percent of the adult population and close to 65 percent for some special groups, such as shift workers and psychiatric patients. Prevalence rates are fairly similar among the countries where insomnia has been studied: England, Finland, Israel and Italy. The number of advertisements for hypnotic drugs in the scientific journals give some idea as to the importance of this disorder as a medical problem.

A significant direct correlation has been found between the Manifest Anxiety Scale score and 1) time required to fall asleep, 2) number of times awake, 3) time required to go back to sleep and 4) report of sleep difficulties. Corresponding daytime complaints typically include fatigue, sleepiness, poor performance, aching muscles, anxiety and loss of concentration and memory. Chronic insomniacs are two and one-half times as likely as non-insomniacs to report vehicle accidents in which fatigue was a factor. One study presented evidence that the complaint of insomnia is an important mortality risk factor. Similarly, clinical experiences support two hypotheses: 1) poor sleep causes drowsiness, poor health and, hence, poor performance, or 2) the complaint of insomnia indicates a person with chronic psychological problems that extend beyond sleep.

Three general types of insomnia have been described: initial, or sleep onset; intermittent, or sleep maintenance; and terminal, or early morning awakening. Several studies suggest that insomniacs are either physiologically or cognitively hyper-aroused relative to normal sleepers. Individuals who are highly aroused may experience difficulty in falling asleep or may awaken frequently at night because sleep is associated with low levels of autonomic arousal. Data from two separate studies support the hypothesis that physiological arousal or anxiety is an etiological factor in insomnia. Insomniacs also seem to be characterized by neuroticism, anxiety, or worry. The results of a complete evaluation of nearly 8000 patients in the Sleep Disorders Clinics (ASDC) across the United States support the conventional hypothesis that insomnia is caused by depression or stress.

Many clinical tests and studies indicate that a substantial subset of people who suffer from insomnia unintentionally promote their condition by the anxiety resulting from their knowledge or misperception that they cannot readily fall asleep. It has also been demonstrated that insomniacs generally underestimate their total sleep time and, more particularly, overestimate the amount of time necessary for them to fall asleep. As a result, the insomniac's problem is perpetuated and causes the insomniac to feel tired the following day.

Common methods of treating insomnia involve the use of prescription drugs or sleep training exercises, or both. For many reasons, a successful sleep training method would be preferred over drug therapy. Thus, a method of sleep training that allows the insomniac to make accurate determinations of time to sleep onset and total sleep time could contribute to the successful reduction or cure of an individual's insomnia.

Well over half of any large population of individuals who complain of insomnia are likely to be using one or more sedative drugs on a daily basis. Although only five percent of insomniacs actually have visited a health professional for their sleep problems, 28 percent use alcohol, 29 percent self-administer over-the-counter medications and 12 percent use both to try to get to sleep. The estimated cost for retail prescriptions of hypnotics in 1970 was $170 million and has increased significantly since that time. In 1991, for example, three sleeping pills, Halcyon, Restoril, and Dalmane accounted for nearly 11 million prescriptions written.

Many hypnotic drugs are ineffective and may cause sleep alterations, especially if consumed in excessive doses over long periods. One study found that initially the following drugs: chloral hydrate, ethcloruznol, glutethimide, methaqualone, methaqualone HCl, and secobarbital were moderately to markedly effective in inducing or maintaining sleep, or both. The study also found, however, that, at the end of a two week period of drug administration, a loss of effectiveness for sleep induction or maintenance, or both, had developed with all these drugs. It is at this danger point where patients begin to increase their dosage or use to try to maintain the same effect. Consequently, the widespread use of hypnotic medication has also made accidental overdosage in people using or abusing these drugs a substantial health hazard. Where drugs are correctly administered, withdrawal of rapidly eliminated benzodiazepine hypnotics can lead to a condition called rebound insomnia. With ultra short half-life drugs, early morning insomnia, another withdrawal phenomenon, may occur even during administration. Additionally, some of these drugs may have unwanted side effects. In 1990, when the Food and Drug Administration tallied the numbers of hostile acts reported in association with 329 different prescription drugs, Halcyon ranked No. 1 followed by Xanax. Ideally, patients with disturbed sleep should be educated not only as to the effectiveness and side effects of prescription drugs, but also to the adverse effects of stimulant pharmacologic agents: cigarette smoking, caffeinated beverages and alcohol.

The use of behavioral techniques in the diagnosis or treatment of insomnia is based on the premise that anxiety or heightened autonomic arousal is an etiological or maintaining factor. Behavioral methods have the additional benefits of the absence of adverse side effects and rebound effects associated with drug treatment, although combination therapy that utilizes behavioral techniques and drug therapy in proper balance can optimize the benefits of both approaches. If heightened physiological arousal or anxiety inhibits sleep, reduction of anxiety or autonomic activity levels would logically facilitate sleep. In this regard, one of the more interesting findings to come out of sleep research is that insomniacs as a group significantly overestimate sleep latencies and underestimate total sleep and sleep efficiency. Overall assessment of sleep by the patient must depend at least partly on the patient's own estimate of sleep duration, which in turn depends on how long the patient takes to fall asleep and how often and for how long the patient remains awake during the night. If the patient is inaccurate in assessing these factors, then the insufficiency of the patient's sleep will, ipso facto, be exaggerated. Following this line of reasoning, several studies suggest that relaxation, systemic desensitization, biofeedback, or other anxiety reducing procedures may be effective in the treatment of insomnia.

Traditional techniques for assessing resting and sleeping patterns and parameters have involved professional monitoring at sleep clinics utilizing equipment to monitor and record brain wave activities, heart rate and other bodily functions. These clinical approaches to diagnosing and treating sleeping disorders can be expensive. Additionally, the clinical environment is typically a dramatic departure from the normal sleeping conditions of the patient and can present not only an inconvenience, but may also contribute to anxiety or discomfort that may be a component of the sleeping disorder. Study of sleeping patterns must typically be undertaken over a week or more to identify consistent patterns and rule out aberrations. Such extended studies in a clinic can compound the expense, inconvenience and associated anxiety for the patient.

For all the expense and complexity that clinical monitoring equipment represent, imprecision still remains. There continues to be debate among those skilled in the art as to the precise definition of sleep onset, and a number of complicated parameters such as the level of alpha wave activity in the brain have been identified as contributing to the measurement of sleep. In fact, sleeping has been characterized as occurring in varying degrees of depth, and such degrees of depth can differ from person to person.

Within this area of uncertainty, generalized, macroscopic determinations of the amount of time a user is in some state of unconscious relaxation corresponding to sleep or the amount of time it takes a user to enter some state of sleep can still be useful in identifying and treating resting pattern problems. Over a six to eight hour period, deviations between measured sleep time from actual sleep time of even several minutes do not offset the informational value of the measurements in revealing to the user his misperceptions about his resting patterns.

SUMMARY OF THE INVENTION

It is therefore an object of the invention to provide a system that is capable of reliably and automatically recording wake time intervals and sleep time intervals during a rest period.

It is another object of the invention to provide a system that can provide useful sleep pattern information without the expense, distraction and inconvenience of clinical probes and professional monitoring.

It is a further object of the invention to provide a timing system for measuring sleep time and wake time intervals that can be used in the comfort of a user's home.

It is still another object of the invention to provide a system for measuring sleep time and wake time intervals that reduces the likelihood of false readings from accidental activation during rest periods.

It is yet another object of the invention to provide a system for measuring sleep time and awake time intervals that additionally assists the user in focusing concentration to enhance relaxation and encourage sleep onset.

It is another object of the invention to provide a system for measuring sleep time and wake time intervals that can be automatically actuated by the user without assistance by another.

These and other objects of the invention are achieved by a timing apparatus that includes a switch controlled timer for recording sleep time of a user, a hand held housing to enclose said timer and a manual contact actuated switch disposed on said housing for contact by the user's hand, said manual contact actuated switch being electrically connected to said timer to prevent the starting of sleep time recording by said timer when said manual contact actuated switch is contacted by the user's hand and to start sleep time recording by said timer when said manual contact actuated switch is released by the user's hand.

This system enables the user to automatically record his sleep time without assistance, for use in the diagnosis or treatment of sleeping disorders by starting the timer when the hand unconsciously relaxes in conjunction with falling asleep. The switch can be any of a variety of types including a galvanic skin response switch that can be controlled by contact with a user's skin, such as at a finger tip. Alternatively, the switch can be a tactile plunger-type switch with a resilient audible, bias similar to that found in computer mouse interfaces.

According to an aspect of the invention, the system is constructed to reduce the likelihood of false readings by making inadvertent switching of the timer difficult and improbable. The switch is preferably disposed on one of a top and bottom side of the housing adjacent a first end of said housing so that the switch can be contacted by a pinching between the thumb and a finger. Upon relaxation of the pinch, the housing is likely to fall away from the hand and reduce the possibility of accidental actuation of the switch that can affect the timer operation.

The housing preferably has a first width across said top and bottom sides at the end where the switch is located. This width reduces to a second width at a second end opposite said first end, whereby the housing provides a relatively larger surface area at the switch for pinching between a finger and thumb and a relatively slender portion for placement between remaining fingers and palm of the user's hand. The housing also preferably has a height between said top and bottom sides that is smaller than said second width, resulting in a slender construction that is readily held and pinched.

The timer can further include an awake timer subsystem for recording awake time when said manual contact actuated switch is contacted. In this manner, the system can provide information as to how long it has taken the user to fall asleep in addition and the time asleep.

Because many users with rest pattern problems awake during the night and have sleep interruptions, it is advantageous for the system to accumulate the time information. To this end, the timer circuitry can include a memory to retain a value of sleep time recorded when said plurality of manual contact actuated switches are concurrently contacted upon awaking during the night. When the user again falls asleep and releases the switch, the timer can be arranged to add an additional value of sleep time recorded to give a cumulative total of separate interrupted sleep intervals.

Similarly, the awake timer subsystem can include a second memory for retaining a value of awake time recorded when said plurality of manual contact actuated switches are concurrently released upon falling asleep and adds an additional value of awake time recorded when said plurality of manual contact actuated switches are again contacted when the user wakes up during a sleep interruption period. The user can cumulatively record elapsed time of separate, awake periods. Of course, if the user is only interested in initial awake time to sleep onset, re-contact during sleep interruptions may not be required.

According to a further aspect of the invention, the timer can be constructed to avoid inadvertent deactivation by the user during sleep such as by unconscious contact with the switch. In a preferred embodiment, the awake timer subsystem can be activated by the concurrent contact of a plurality of switches. The switches can be of different types, such as a galvanic skin response switch and a tactile plunger-type switch.

The awake time interval recorded by the awake timer subsystem need not be limited to a single occurrence. The system can be configured so that the user can re-contact the switches at the time of each waking occurrence throughout the night and continue recording of cumulative awake time. The timer can re-start wake time measuring, not from a "zero" time, but from the point that the device halted after the first onset of sleep. The device halts awake time measuring again at each subsequent release of any switch in conjunction with onset of sleep. Accordingly, in the morning, the timer can easily provide total sleep time intervals and total wake time intervals during a night.

The device can also be equipped with a leash permitting complete and easy release of the housing when the user falls asleep while still securing the device in proximity to the user's hand to enable the user to easily retrieve the device, for example, when the user awakens during the night and must re-contact the switches on the device to restart recording of awake time.

The device can also include a visual and/or an auditory confirmation alarm to alert the user that all the switches have contacted and that the device is recording awake time or is configured to record sleep time upon release of a switch. Another aspect of the invention includes a delay in the timer circuit that prevents the timer from recording awake time until the switches are been concurrently closed for a predetermined wait time (for example, three sounds) to prevent brief and inadvertent concurrent contact with the switches to initiate recording of awake time.

BRIEF DESCRIPTION OF THE DRAWINGS

There are shown in the drawings embodiments of the invention that are presently preferred, it being understood, however, that the invention is not limited to the precise arrangements and instrumentalities shown, wherein.

DETAILED DESCRIPTION OF PREFERRED EMBODIMENTS

The present invention is directed to a sleep pattern timing apparatus for use in enabling a user to measure sleep time and awake time during resting periods without the assistance of another. The device can be used to obtain rest pattern information for use in the diagnosis or treatment of insomnia by measuring sleep time and awake time necessary before the onset of sleep. Observation of these measurements can assist in correcting an insomniac's overestimation of sleep latency and an insomniac's underestimation of total sleep and sleep efficiency.

It should be appreciated that the timing apparatus of the invention is directed to the recording of events in connection with a user's resting patterns during a given "resting period." Resting period is not the time actually sleeping, but in lay vernacular, extends from when the user "goes to bed" until he is "up for the day." Of course, some users go to sleep in a chair or in environs other than a bed. Some users, such as shift workers, may sleep in the day and spend most of their alert hours in the evening or night. Thus, more technically, resting period extends from the time the user retires to a resting position and attempts to fall asleep until the user wakes up and intends to remain awake for a substantial period. For most users, the relevant resting period will span between six to ten hours.

While the timing system is intended for measuring either the amount of time it takes the user to fall asleep (referred to as "awake time") or the amount of time the user is asleep (referred to as "asleep time"), it is important to note that the system is intended only to measure the elapsed time of events to a reasonable degree of accuracy and precision relative to the total resting period. Within the typical time frame of several hours, it is not critical for the timing system to measure precisely to the second or even minute when sleeping actually begins.

Thus, references to sleep time and awake time are used in a macroscopic sense relative to a total resting period spanning several hours. These references are not intended to, nor need they, precisely correspond to actual periods of sleep and awake states that are themselves subject to different interpretations and definitions.

Figure 1:
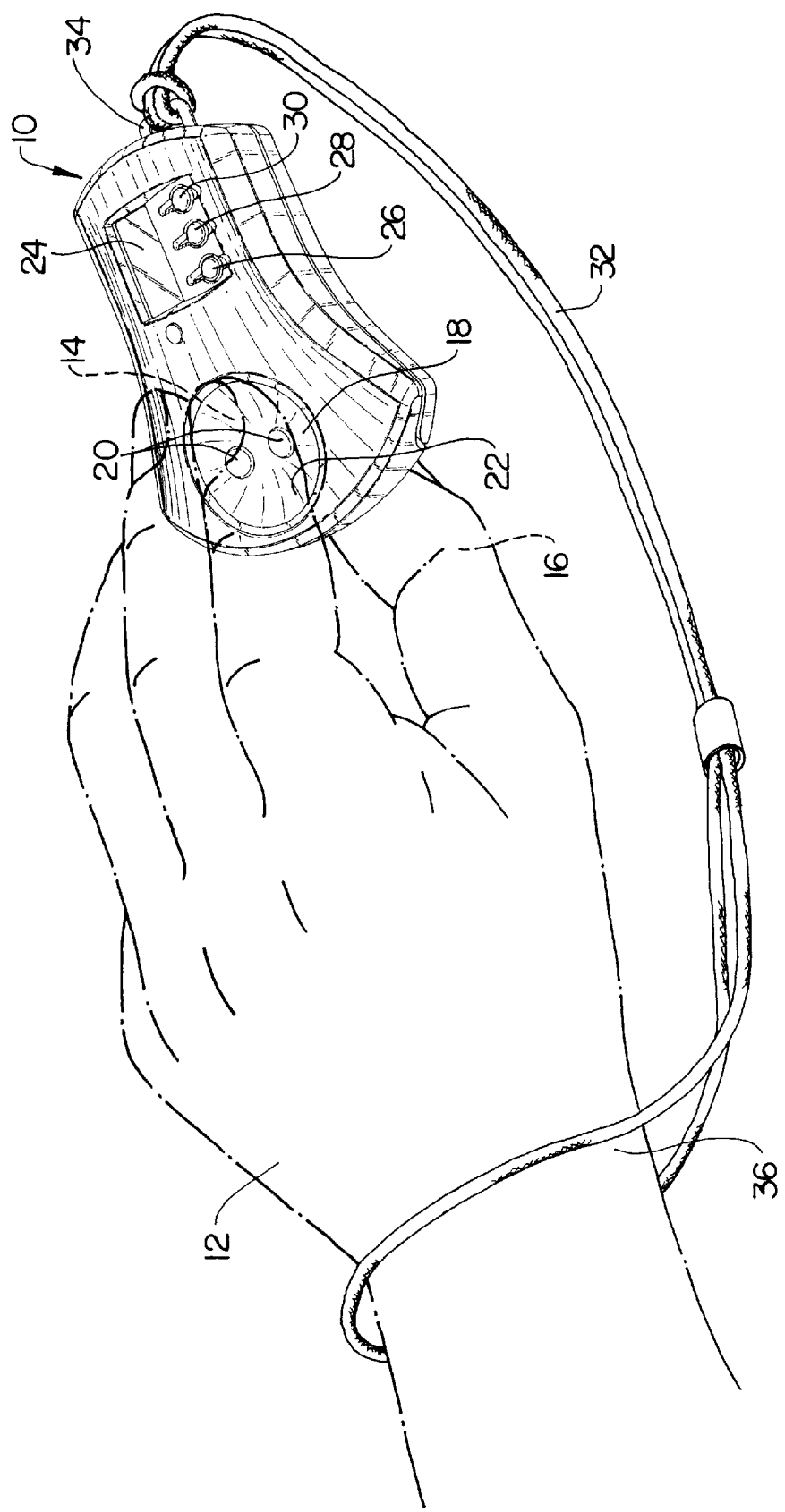
FIG. 1 is a perspective view of a preferred construction embodying the invention as held in a pinching position by a user's hand.

Referring to FIG. 1, a sleep pattern timing apparatus according to the invention can include a timer circuit enclosed in a housing, such as a housing 10 sized and constructed to be held by a user's hand 12, and particularly pinched between a finger tip 14 and thumb tip 16 of the hand 12. As used throughout, reference to a hand is intended to include its fingers, thumb and palm. Although not preferred, the system can be adapted for positioning between the fingers, thumbs and/or palms of both of the user's hands. At least one switch, such as a galvanic skin response switch 18, is disposed on the housing 12 and externally accessible for contact by the user to control operation of the timer. The galvanic skin response switch 18 can provide two lead terminals 20 that are electrically connected or shorted by the user's skin to activate the switch 18 in known manner. The lead terminals 20 are preferably positioned in a recess 22 so that contact with the user's skin generally requires a conscious positioning of a finger 14 into the recess 22 to contact the switch 18.

The timer is electrically connected to the switch 18 so that, at a minimum, sleep time or time to sleep onset is measured as a function of whether the switch 18 is contacted or released. When the switch 18 is contacted as shown, the recording of sleep time by the timer circuit is prevented. The continued contact with the switch 18 requires a conscious pinching contact that is accomplished by the user while awake.

In addition to preventing the recording of sleep time, the continuous pinching of the switch 18 provides a focus point for the user to concentrate. This focused concentration can contribute to relaxation, alleviating the so-called "racing mind," and assist the user in falling asleep quicker.

As the user falls asleep, the pinching contact is relaxed and the switch 18 is released. The released switch 18 causes the timer circuit to begin recording time corresponding to the user's sleep interval. The housing 10 is preferably held in the pinching configuration so that the timing apparatus can fall away from the user's finger 14 to reduce the possibility of continued contact of the switch 18 after the user has fallen asleep.

The time the user is awake during the rest period can also be monitored, either alone or in conjunction with measurement of sleep time. One important time interval to measure during a rest period, particularly for noting the effectiveness of drugs in combination therapy, is the time to sleep onset. This period begins when the user assumes a resting position, that is "goes to bed," and ends when he falls asleep. This period is referred to throughout as "awake time." Other awake times also occur during the rest period when the user awakes during sleep interruptions, and all such awake periods will be referred to as awake time. Where a distinction is needed, the first period of attempting to fall asleep is referred to an initial awake time.

The housing 10 can further provide a display, such as a LCD display 24, to show information such as time values generated by the timer. A series of control buttons 26, 28, 30 can also be mounted on the housing 10 to provide various control functions to the timer apparatus.

The timing apparatus is preferably secured to the user so that the apparatus can easily be retrieved when the user awakes. In the illustrated embodiment, a leash 32 is connected to an attachment buckle 34 formed at one end of the housing 10. The leash 32 can be looped around the user's wrist 36 and selectively tightened, using a slider 38. The easy retrieval provided by the leash 32 enhances the ability to use the fall away feature of the device as a fail safe against inadvertent switching.

Figure 2:
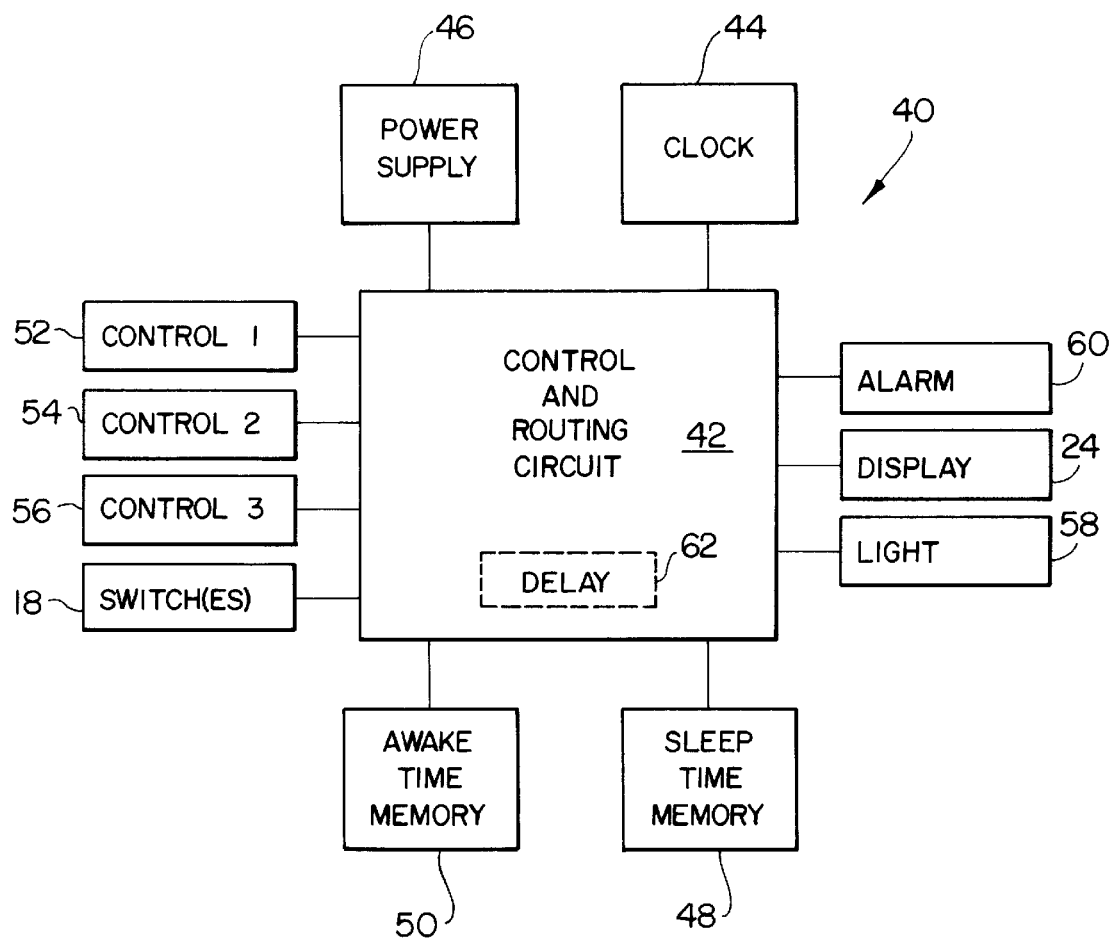
FIG. 2 is a functional schematic of a timer circuit for use in the timing apparatus.

Referring to FIG. 2, a timer circuit 40 within the housing generally includes control and routing circuitry 42 for obtaining, storing and displaying time information generated by a clock circuit 44. The timer circuit 40 is powered by a power supply 46. The timer circuit 40 preferably includes a sleep time memory 48 for storing time count information from the clock 44. The control and routing circuit 42 can be configured using known techniques so that the time count generated by the clock 44 is prevented from being stored in the sleep time memory 48 when the switch 18 is contacted. When the switch 18 is released, the control and routing circuit 42 stores the time count from the clock 44 in the sleep time memory 48.

The timer circuit preferably includes an awake timer subsystem. The control and routing circuitry 42 can be configured to store time count information from the clock 44 in an awake time memory 50 when the switch 18 is contacted and to discontinue storing time in the awake time memory 50 when the switch 18 is released. In this preferred construction, the time count information from the clock 44 is alternately stored and accumulated in each of the awake time memory 50 and the sleep time memory 48 as a function of whether the switch 18 is contacted or released, which generally corresponds to whether the user is awake and consciously contacting the switch 18 or has fallen asleep and has released the switch 18, respectively. An alternative system could provide measurement of only awake time, without recording sleep time intervals.

In an alternative embodiment, a plurality of additional memories (not shown) can be provided to separately store time counts for a number of separate intervals during the rest period. In this way, the control and routing circuit 42 can be configured to separately store the initial wake time, the first sleep period, the awake time during a first sleep interruption, the second sleep period, and so on.

The sleep time and awake time information can be shown on the display 24. The actual time count at the moment—be it sleep time or awake time—is preferably displayed as the system is being used. Thus, the control and routing circuit 42 can be configured to display the value of the awake time memory 50 or the sleep time memory 48 as it is being simultaneously updated. While the time can be displayed in different levels of detail, the timer circuit 40 preferably displays only hours and minutes because the seconds are not critical in the multiple hour time frame of the total rest period.

A series of controls 52, 54, 56 are preferably included in the timer circuit 40 and can be actuated, for example, by the control switches 26, 28, 30(SEE FIG. 1). The controls 52, 54, 56 can generally manage the display, activation, and deactivation of the timer circuit 40.

The controls can each be configured with the control and routing circuit to provide dual control signals. A first signal and function can be provided when the control is briefly actuated and released (say, within three seconds), and a second signal and function when the control is actuated for an extended period, for example, three seconds or more.

The first control 52, when actuated for three seconds, can act as a master start for the timer circuit 40. This function can connect the power supply 46 to the control and routing circuit 42 and start initial operations, such as displaying a zero time count on the display 24 as well as some other display indicia that the circuit is ready. The clock 44 can also be powered to generate a time count without the time count value being routed to either the display, or either of the memories. The first control, when actuated briefly, can show on the display the total awake time as stored in the awake time memory at any given moment.

The second control 54, when actuated for three seconds, can reset the time count values in the memories to zero. This function can be used, for example, in the morning to clear the time values just noted. The second control 54, when actuated briefly, can stop all time recording and "freeze" the values in the memories.

The third control 56, when actuated for three seconds, can power down the timer circuit by disconnecting the power supply. The third control, when actuated briefly, can cause the total sleep time value in the sleep time memory to be displayed at any given moment. Alternative and additional control functions can also be provided.

A confirmation light 58 can also be placed within the timer circuit. The confirmation light 58 can, for example, be configured to blink when the switch 18 is contacted, signaling the beginning of awake time recording. The confirmation light 58 provides the user with a visual cue that the user has properly contacted the switch.

An audible alarm 60 can also be integrated with the timer circuitry. The alarm 60 is preferably activated at the moment the switch is contacted. The alarm 60 provides the user with an auditory cue that the user has properly contacted the switch and the timer circuit is recording awake time.

The timer circuit 40 preferably includes a delay 62 for briefly postponing, for 3 seconds or more, the transition between awake time recording and sleep time recording, and vice versa. This delay reduces the occurrences of inadvertent transitions. If the user accidentally releases the switch during an awake time interval, or the device is bumped from her hand somehow, the delay enables her to re-contact the switch within three seconds without affecting the time recording status of the timer circuit. Similarly, during sleep time recording, the delay 62 can prevent the transition to awake time if the switch is briefly contacted by chance during an unconscious movement of the user's hand.

It should be noted that the timer circuit arrangement described is just one embodiment, and other alternative arrangements are possible. For example, a simplified system could be limited to measuring only sleep time or only awake time, even just initial awake time. The time measurement could be displayed directly from the clock without parallel storage in a memory. Thus, the scope of the invention should not be considered limited to the described circuit.

Figure 3:
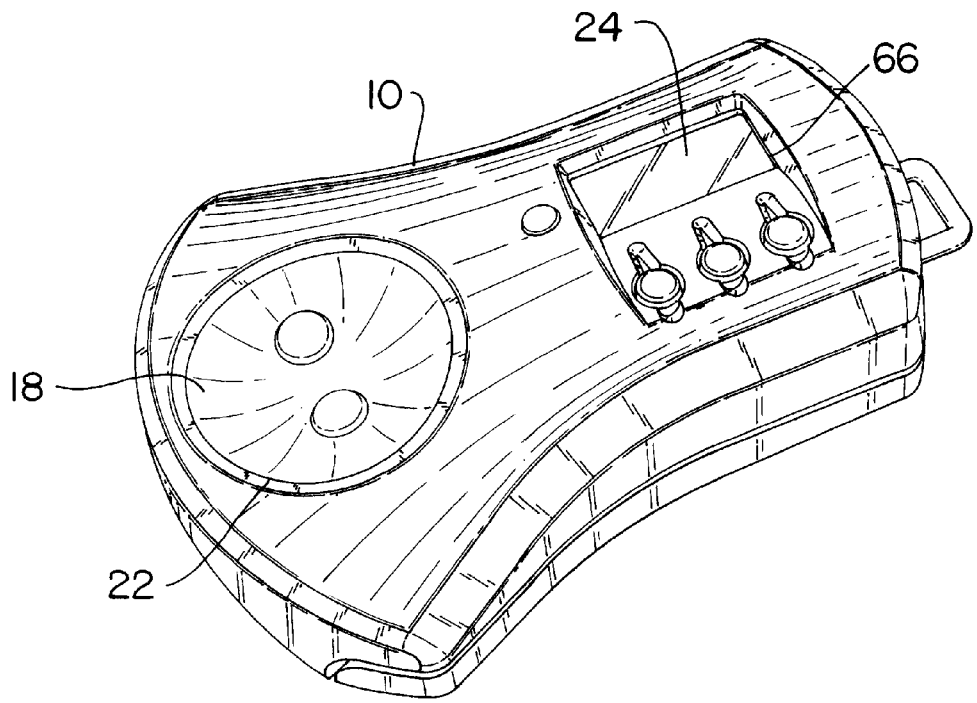
FIG. 3 is a right front top perspective view of a timing apparatus according to the invention.
Figure 4:
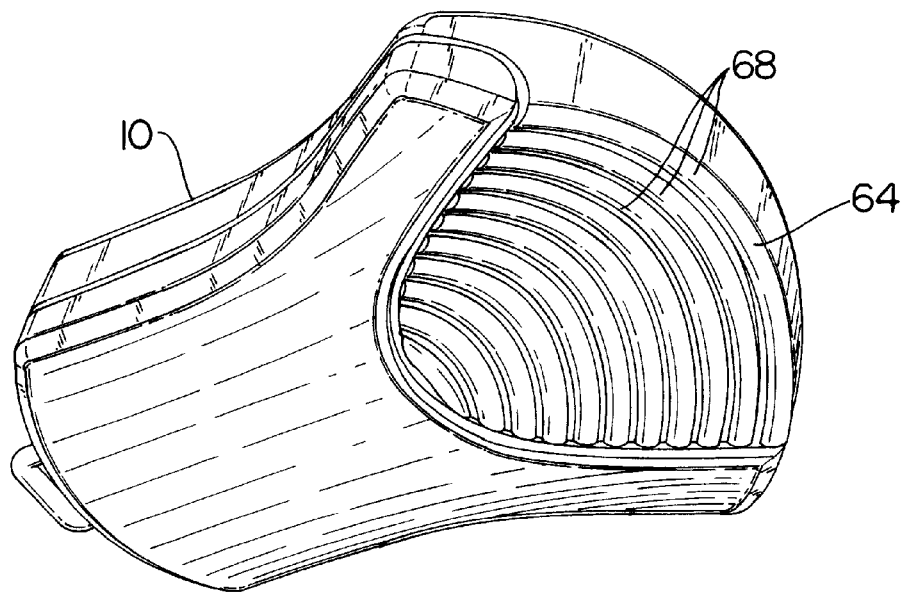
FIG. 4 is a left front bottom perspective view of FIG. 3.

As shown in FIGS. 3 and 4, the timing apparatus preferably includes a plurality of switches 18, 64 electrically connected in series to the timer circuit internalized in the housing. Significantly, this feature prevents inadvertent actuation of the electronic circuit by the user because the circuit will be broken until all the switches are closed. Thus, if the user accidentally closes one switch, but not all switches, the timer circuit will not be affected. The presently preferred number of switches is two.

When both switches 18, 64 are contacted, the timer circuit is activated to begin recording awake time. The timer continues recording of awake time until the series is broken by the release of at least one switch.

The wake time interval recorded by the awake timer subsystem of the timer need not be limited to a single occurrence. Upon reawakening, but before the user's intended wake time, the user can concurrently contact the switches 18, 64. By contacting the switches, the timer stops recording sleep time and the awake timer subsystem restarts recording awake time, not from a "zero" time, but from the point that the awake timer halted after the first onset of sleep. The awake timer subsystem stops recording of waking time at each subsequent onset of sleep. Thus in the morning, the timer has recorded the total awake time interval and the total sleep time interval.

The display 24 can be located within a display recess 66. Also located within the display recess 66 are the three control switches 26, 8, 30 embedded within control switch indentations. Because the control switches are embedded within the control switch indentations, inadvertent activation of the switches is minimized.

The switches 18, 84 can be arranged in a variety of manners to be released upon falling asleep. In a preferred embodiment, the switches are any switches that can be activated by compression between the thumb and finger of the user. When the compression is released, for example when the user's hand is relaxed upon falling asleep, the switches are deactivated.

The presently preferred first switch is a galvanic skin response switch 18. The galvanic skin response switch 18 is located within a depression 22 on the housing. The depression allows the user to easily locate the galvanic skin response switch 18 to ensure that the user properly contacts the galvanic skin response switch when desired. The presently preferred second switch is a tactile switch 64. The tactile switch 64 is activated when pressure is applied and continues to be activated until the pressure is released. The tactile switch 64 is located opposite the galvanic skin response switch on the housing. The tactile switch is covered with ridges 68 to allow the user to easily locate the tactile switch.

The timing apparatus relies upon the unconscious and natural separation or relaxation of the user's thumb and fingers when the user reaches a certain state of relaxation to control the recording of awake time and sleep time. Upon onset of sleep, the thumb and fingers of the user's hand relax, and thus, release the pressure that keeps the switches closed. As previously mentioned, when at least one of the switches is open, recording of awake time ends.

The exact point in time at which any person falls asleep is debated by those knowledgeable in the field. The physiological process of falling asleep differs from one person to the next, so a determination of when one person falls asleep may not necessarily work for all persons. Though the process of falling asleep can vary greatly from one person to the next, variance of the process within a single person is less. By using the unconscious and natural separation of the user's thumb and fingers, general determination of the time at which the onset of sleep begins can be determined. Thus, by using the natural separation of the thumb and fingers to stop the recording of awake time, a repeatable baseline event can be established from which subsequent recordings can be compared.

The following example is shown to illustrate use of the invention. Before the user lies down for sleep, the user holds down the left control switch to initialize the timer. As the user lies down for sleep at 12:00 midnight, the user pinches the switches between the user's finger and thumb, and thus, contacts the switches that initiates the recording of awake time by the awake timer subsystem. The user's hand is preferably positioned so as not to be restrained under a pillow or the user's body that would impede separation of the pinch. The switches, however, are configured to account for this possibility by having sensitivity adjusted so that the slightest relaxation of the pinch results in either a release of the plunger type switch or separation from the galvanic skin response switch, either of which results in a change in the timer circuitry.

At 12:50 am, the user falls asleep. Upon onset of sleep, the thumb and fingers of the user's hand relax and separate, and thus, release the pressure that keeps the switches closed. As previously mentioned, when at least one of the switches is opened, recording of awake time by the first timer subsystem ends and recording of sleep time timer begins. When the user wakes up at 8:00 am, the user can instantly review the total sleep time, shown preferably in hours and minutes or he can briefly hold down the middle control switch or can pinch the switches again to stop recording of sleep time.

To review awake time, the user can simply contact all switches to change the display to the awake time mode or the user can briefly hold down the left control switch to show on the display the total awake time, which in this example is fifty minutes. To review sleep time, the user briefly holds down the right control switch to show on the display the total sleep time, which in this example was seven hours and ten minutes.

In situations when the user awakes more than once during the night, the same method can still be used. The user can re-initiate recording of awake time immediately upon each waking occurrence and, upon each subsequent falling asleep, the recording of waking time will automatically stop and the recording of sleep time will resume. Therefore, the time period that can be observed on the readout display of the timing apparatus at the end of the night can be the sum total of all wake time intervals or all the sleep time intervals throughout the entire night.

The following example is shown to illustrate the applied method with multiple waking occurrences. On Jan. 2, 1995, before the user lies down for sleep, the user holds down the left control switch to initialize the timer. As the user lies down for sleep at 12:00 midnight, the user pinches the switches between the user's fingers and thumb, and thus, closes the switches which initiates the recording of awake time by the awake timer subsystem. At 12:30 am, the user falls asleep. Upon onset of sleep, the thumb and fingers of the user's hand relax, and thus, release the pressure that keeps that switches closed.

When the user awakes at 2:30 a.m., according to the method, the user re-initiates awake time measurement by pinching the switches between the user's fingers and thumb which also stops of sleep time by the timer. When the user falls asleep at 3:00 am, the thumb and fingers separate, which causes the of awake time to stop and the of sleep to resume. The wake lapse time at this point is one hour. This process is repeated when the user awakes at 4:00 am and falls asleep at 4:15 am. When the user wakes up at 8:00 am, the user briefly holds down the middle control switch to stop recording of sleep time by the second timer subsystem.

To review awake time, the user briefly holds down the left control switch to show on the display the total awake time, which in this example was one hour and fifteen minutes. To review sleep time, the user briefly holds down the right control switch to show on the display the total sleep time, which in this example was six hours and forty five minutes.

The steps as outlined above may be repeated over a period of nights at the user's choosing. Where all of the above time instances and intervals are recorded over a period of days, weeks, months, or years, the user can track average or increased performance of total time asleep during the night, and wake lapse time. Then the user would realize a positive performance result for application of the invention.

Therefore, the invention provides a user with an economical, self-administered, comfortable apparatus for treating a user's overestimation of sleep latency and underestimation of total sleep and sleep efficiency. The invention furnishes a user with a sleep training method that allows accurate determinations of wake time during each night, and, therefore, total sleep time over a period of days or weeks, or even longer.

A variety of switch types and electrical configurations, whether now known or later developed, can be use to implement the invention. Preferred embodiments have been described with reference to the combination of a plunger type switch and a galvanic skin response switch. What is important to the invention is that two or more switches are arranged electrically relative to each other and to the timer so that the timer is placed into one mode—either starting timing or stopping timing—when all of the switches are contacted, and is switched to the opposite mode—either stopping timing or starting timing—when any of the switches is released.

The electrical arrangement can include a series connection of the switches to each other between the timer and a power supply so that a complete closing of all switches in the series is required for the timer to start timing and an opening of any switch results in stopping the timing operation. More sophisticated timing control circuitries will now be understood to those skilled in the art.

As used in the specification and claims, contacting the switch is intended to mean a touching of the switch somewhere on its assembly by the user that effects a change in the state of the switch. Depending upon the nature of the switch and its design, the contact may be ever so slight or it may be a relatively high pressure compression.

Similarly, releasing the switch connotes a change in the contact with the switch that results in a change in the switch state. The release may be a complete disengagement with the switch componentry or it may a relaxation of the degree of pressure placed on the switch without actual disconnection, depending upon the nature of the switch and its design.

Contacting a switch may result in closing a circuit, and releasing a switch may result in opening a circuit, but the terminology is not intended to be limited as such. There could be an electrical configuration in which the switch contact and release change connection of a circuit lead between two circuit paths rather than create an open and closed circuit.

While specific embodiments of the invention have been set forth with a relatively high degree of particularity, it is intended that the scope of the invention not be so limited. Instead, the proper scope of the invention may include alternatives which are now within the purview of one skilled in the art. Thus, the scope should be ascertained by a reading of the claims that follow.

What is claimed is:

1. A sleep pattern timing apparatus, said apparatus comprising: a timer for recording sleep time of the user;
    a housing to enclose said timer, said housing being sized to be hand held; and
    a plurality of manual contact actuated switches, each switch being disposed separately on said housing so one of said switches can be contacted by a finger on a user's hand and another of aid switches can be contacted by another part of the user's hand, said plurality of manual contact actuated switches being electrically connected to said timer to control the stopping of sleep time recording by said timer when each of said plurality of manual contact actuated switches are contacted by a hand of the user and to control the starting of sleep time recording by said timer when any of said plurality of manual contact actuated switches is released;
    whereby the user can automatically record his sleep time without assistance for use in the diagnosis or treatment of sleeping disorders.

2. An apparatus as recited in claim 1, wherein said plurality of manual contact actuated switches includes a first switch and a second switch opposing each other on said housing, whereby said first switch and said second switch can each be actuated by a pinching contact between the user's thumb and a finger.

3. An apparatus as recited in claim 2, wherein said first switch is a galvanic skin response switch.

4. An apparatus as recited in claim 3, wherein said second switch is a tactile plunger-type switch.

5. An apparatus as recited in claim 1, wherein said timer includes an awake timer subsystem for recording of awake time when all of said plurality of manual contact actuated switches are contacted.

6. An apparatus as recited in claim 5, further comprising an audible alarm electrically connected to the timer for confirming to the user that said awake timer subsystem has started recording awake time.

7. An apparatus as recited in claim 5, further comprising a visual confirmation means for confirming to the user that said timer has started recording awake time.

8. An apparatus as recited in claim 1, further comprising a leash for securing said housing to the user.

9. An apparatus as recited in claim 1, wherein said timer includes a delay for preventing said timer from starting the recording of sleep time until one of said plurality of manual contact actuated switches is released for a predetermined wait time and for preventing said timer from stopping the recording of sleep time until said plurality of manual contact actuated switches are concurrently contacted for a second predetermined wait time.

10. An apparatus as recited in claim 1, further comprising a reset button disposed on said housing and electrically connecting to the timer to reset the timer to zero, wherein said timer includes a memory to retain a value of sleep time recorded when said plurality of manual contact actuated switches are concurrently contacted and adds an additional value of time recorded when said plurality of manual contact actuated switches are again released, whereby the user can cumulatively record elapsed time of separate, interrupted sleep periods.

11. An apparatus as recited in claim 10, wherein said awake timer subsystem includes a second memory to retain a value of awake time recorded until said plurality of manual contact actuated switches are concurrently released and adds an additional value of awake time recorded when said plurality of manual contact actuated switches are again contacted, whereby the user can cumulatively record elapsed time of separate, awake periods.

12. An apparatus as recited in claim 1, wherein said housing has a height between said top and bottom sides, said height smaller than said second width.

13. An apparatus as recited in claim 1, wherein said plurality of manual contact switches are disposed on one of a top and bottom side of the housing adjacent a first end of said housing, said housing having a first width across said top and bottom sides at said first end, said first width reducing to a second width at a second end opposite said first end, whereby the housing provides a relatively larger surface area at the switch for pinching between a finger and thumb and a relatively slender portion for placement between remaining fingers and palm of the user's hand.

14. A sleep pattern timing apparatus, said apparatus comprising: a timer for recording awake time of the user;

a housing to enclose said timer, said housing being sized to be hand held; and a plurality of manual contact actuated switches, each switch being disposed separately on said housing so one of said switches can be contacted by a finger on a user's hand and another of said switchs an be contacted-by another part of the user's hand, said plurality of manual contact actuated switches being electrically connected to said timer to control the starting of awake time recording by said timer when each of said plurality of manual contact actuated switches are contacted by a hand of the user and to control the stopping of awake time recording by said timer when any of said plurality of manual contact actuated switches is released;

whereby the user can automatically record his sleep time without assistance for use in the diagnosis or treatment of sleeping disorders.

15. An apparatus as recited in claim 14, wherein said plurality of manual contact switches are disposed on one of a top and bottom side of the housing adjacent a first end of said housing, said housing having a first width across said top and bottom sides at said first end, said first width reducing to a second width at a second end opposite said first end, whereby the housing provides a relatively larger surface area at the switch for pinching between a finger and thumb and a relatively slender portion for placement between remaining fingers and palm of the user's hand.

16. An apparatus as recited in claim 15, wherein said housing has a height between said top and bottom sides, said height smaller than said second width.

17. An apparatus as recited in claim 14, wherein said plurality of manual contact switches are galvanic skin response switches.

18. An apparatus as recited in claim 14, wherein said plurality of manual contact switches are tactile plunger-type switches.

19. An apparatus as recited in claim 14, wherein said timer includes an awake timer subsystem for recording awake time when said plurality of manual contact actuated switches are contacted.

20. An apparatus as recited in claim 14, further comprising a leash for securing said housing on the user, whereby said housing can be readily retrieved for further use during sleep interruptions.

* * * * *